(12) United States Patent
Husen et al.

(10) Patent No.: US 8,013,192 B2
(45) Date of Patent: Sep. 6, 2011

(54) PROCESS FOR PREPARING 1,3-PROPANEDIOL

(75) Inventors: Douglas Lee Husen, Prairieville, LA (US); Glenn Charles Komplin, Katy, TX (US); Joseph Broun Powell, Houston, TX (US); Paul Richard Weider, Houston, TX (US)

(73) Assignee: Shell Oil Company, Houston, TX (US)

( * ) Notice: Subject to any disclaimer, the term of this patent is extended or adjusted under 35 U.S.C. 154(b) by 944 days.

(21) Appl. No.: 11/950,294

(22) Filed: Dec. 4, 2007

(65) Prior Publication Data

US 2008/0154071 A1  Jun. 26, 2008

Related U.S. Application Data

(60) Provisional application No. 60/868,672, filed on Dec. 5, 2006.

(51) Int. Cl.
*C07C 27/20* (2006.01)
*C07C 27/04* (2006.01)
*C07C 29/36* (2006.01)

(52) U.S. Cl. ........ 568/867; 568/862; 568/882; 568/852; 568/854

(58) Field of Classification Search ................ 568/867, 568/862, 882, 852, 854
See application file for complete search history.

(56) References Cited

U.S. PATENT DOCUMENTS

| 3,687,981 A | 8/1972 | Lawrence et al. .......... 260/340.7 |
| 5,463,145 A | 10/1995 | Powell et al. ................. 568/867 |
| 6,284,930 B1 | 9/2001 | Haas et al. .................... 568/491 |
| 2002/0010378 A1 | 1/2002 | Kakimoto et al. ............ 568/867 |

FOREIGN PATENT DOCUMENTS

JP      2002155000      5/2002

OTHER PUBLICATIONS

Ramesh K. Shah and Alfred C. Mueller, "Ullmann's Encyclopedia of Industrial Chemistry—Heat Exchange," Jun. 15, 2000, Wiley-VCH Verlag GmbH & Co., kGaA, Weinheim, XP002475727, pp. 1-25.

*Primary Examiner* — Elvis O Price

(57) ABSTRACT

The invention provides a process for preparing 1,3-alkanediols, such as 1,3-propanediol (PDO), from 3-hydroxyaldehydes, such as 3-hydroxypropanal (HPA), comprising providing a mixture of 3-hydroxyaldehydes in an organic solvent; extracting into an aqueous liquid a major portion of the 3-hydroxyaldehydes to provide an aqueous phase comprising 3-hydroxyaldehydes in greater concentration than the concentration of 3-hydroxyaldehydes in the 3-hydroxyaldehyde mixture, and an organic phase; separating the aqueous phase from the organic phase; contacting the aqueous phase with hydrogen in the presence of a hydrogenation catalyst to provide a hydrogenation product mixture comprising 1,3-alkanediols and water; separating water from the 1,3-alkanediols using a multi-effect evaporation scheme; recycling water containing about 50 wt % or less 1,3-propanediol based upon the total amount of 1,3-propanediol and water to the extraction stage; and recovering 1,3-alkanediols.

28 Claims, 5 Drawing Sheets

PROCESS FOR PREPARING 1,3-PROPANEDIOL

This application claims the benefit of U.S. Provisional Application No. 60/868,672 filed Dec. 5, 2006, which is incorporated by reference.

FIELD OF THE INVENTION

This invention relates to a process for preparing 1,3-propanediol (PDO). In particular the invention relates to such a process with improved heat recovery.

BACKGROUND OF THE INVENTION

The hydroformylation of oxiranes to produce 3-hydroxyaldehydes has been discussed in "New Syntheses with Carbon Monoxide" edited by J. Falbe (1980), pp. 131-132. The reaction is catalyzed with a cobalt-based catalyst, or a phosphine-modified cobalt-based catalyst. The hydroformylation product, be it the 3-hydroxyaldehyde or the cyclic hemiacetal (its dimer) may be converted into a 1,3-alkanediol by hydrogenation. This process is of particular importance to the preparation of 1,3-propanediol (PDO), an intermediate in the production of polytrimethylene terephthalate for fibers and films, that may be prepared by hydrogenating 3-hydroxypropanal (HPA).

U.S. Pat. No. 5,463,145 describes a process for producing the hydroformylation product at improved rates. The process utilizes water as the extraction solvent, cobalt in the catalyst and a promoter which is a lipophilic quaternary salt of a Group V element. The catalyst and promoter are conveniently recycled with the organic phase which readily separates from the water extraction solvent and is then recycled to the hydroformylation stage. Unfortunately, water has a high heat of vaporization which makes the cost of separating water from the 1,3-alkanediol product in this process considerably higher than such cost in conventional petrochemical processes which use solvents with lower heats of vaporization. Also, the water must be purified to be recycled to the extraction stage because the presence of PDO can cause loss of the hydroformylation catalyst and/or the promoter and the presence of light ends such as ethanol can cause other problems with the hydroformylation catalyst and/or the promoter.

It would be advantageous to reduce the energy required to separate the excess water and find a way to reuse the water in the extraction stage without expensive purification.

SUMMARY OF THE INVENTION

In one aspect, the present invention provides a process for preparing a 1,3-alkanediol from a 3-hydroxyaldehyde, comprising providing a mixture of a 3-hydroxyaldehyde in an organic solvent; extracting into an aqueous liquid a major portion of the 3-hydroxyaldehyde to provide an aqueous phase comprising the 3-hydroxyaldehyde in greater concentration than the concentration of the 3-hydroxyaldehyde in the 3-hydroxyaldehyde mixture, and an organic phase; separating the aqueous phase from the organic phase; contacting the aqueous phase with hydrogen in the presence of a hydrogenation catalyst to provide a hydrogenation product mixture comprising a 1,3-alkanediol and water; separating water from the 1,3-alkanediol using a multi-effect evaporation scheme; recycling water containing about 50 wt % or less of the 1,3-alkanediol based upon the total amount of the 1,3-alkanediol and water to the extraction stage; and recovering the 1,3-alkanediol.

In another aspect, the present invention provides a process for preparing 1,3-propanediol comprising the steps of:

(a) providing a mixture of 3-hydroxypropanal in an essentially non water miscible organic solvent;

(b) adding an aqueous liquid to said mixture and extracting into said aqueous liquid a major portion of the 3-hydroxypropanal to provide an aqueous phase comprising 3-hydroxypropanal in greater concentration than the concentration of 3-hydroxypropanal in the 3-hydroxypropanal mixture, and an organic phase;

(c) separating the aqueous phase from the organic phase;

(d) contacting the aqueous phase with hydrogen in the presence of a hydrogenation catalyst to provide a hydrogenation product mixture comprising 1,3-propanediol, water, and light ends;

(e) separating water from the hydrogenation product mixture by introducing the hydrogenation product mixture into a first thermal separation stage and heating it to produce a first overhead hot vapor stream comprising water and light ends and a first bottoms thermal separation product mixture stream comprising water and 1,3-propanediol in greater concentration than the concentration of 1,3-propanediol in the hydrogenation product mixture;

(f) introducing the first bottoms thermal separation product mixture stream into a second thermal separation stage to produce a second overhead hot vapor stream comprising water and light ends and a second bottoms thermal separation product mixture stream comprising water and 1,3-propanediol in greater concentration than the concentration of 1,3-propanediol in the first bottoms thermal separation product mixture stream;

(g) optionally repeating step f) at least once to produce a third or successive overhead hot vapor stream comprising water and light ends and a third or successive bottoms thermal separation product mixture stream comprising water and 1,3-propanediol in greater concentration than the concentration of 1,3-propanediol in the preceding bottoms thermal separation product mixture stream;

(h) removing the heat from at least one of the overhead hot vapor streams and providing said heat for use in at least one of the other steps of the process for preparing 1,3-propanediol, preferably a thermal step, preferably by heat exchange with a lower temperature process stream and/or by accompanying transfer of latent heat by condensation;

(i) optionally introducing the last bottoms thermal separation product mixture stream to a crude 1,3-propanediol separator, such as a thermal separator including, for example, a distillation column, flasher or evaporator, to produce a crude 1,3-propanediol overhead stream comprising water, 1,3-propanediol, and light ends, and a crude 1,3-propanediol bottoms stream comprising water and 1,3-propanediol in greater concentration than the concentration of 1,3-propanediol in the last bottoms thermal separation product mixture stream;

(j) optionally introducing the crude 1,3-propanediol overhead stream into a light ends separator, for example a thermal separator such as a distillation column, stripper, or evaporator, to remove light ends, such as, for example, any ethanol coproduct, from the water and 1,3-propanediol, thereby producing a concentrated water stream containing about 50 wt % or less 1,3-propanediol based upon the total amount of 1,3-propanediol and water;

(k) recycling the concentrated water stream to step b); and
(l) recovering 1,3-propanediol from the crude 1,3-propanediol bottoms stream.

By far, most of the heat from step h) is transferred by condensing steam. A small amount is transferred by cooling steam as a vapor from, for example, 120° C. to 100° C., but the majority of the heating effect is provided by phase change in condensing steam to transfer the latent heat of vaporization.

In a preferred embodiment of the invention, a multiple effect evaporation scheme is used to remove water from the 1,3-propanediol to produce more highly concentrated 1,3-propanediol mixtures which can be further purified using conventional thermal separation equipment including distillation columns, flashers, evaporators, or extraction steps. In an embodiment, the first thermal separator and the crude 1,3-propanediol distillation column are the stages of "effects" in a multi-effect evaporation scheme.

DETAILED DESCRIPTION OF THE INVENTION

Figure 1:
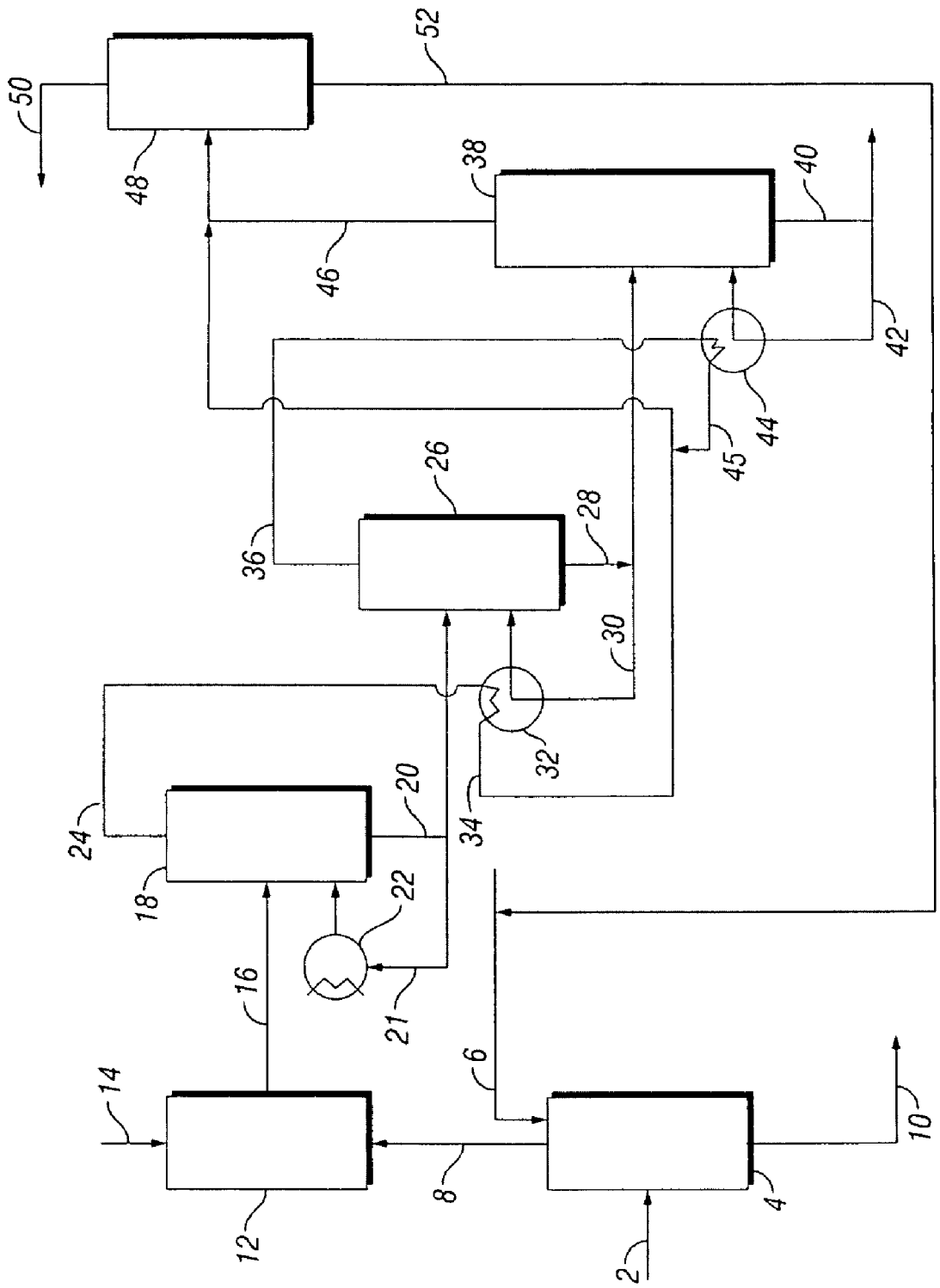
FIG. 1 is a flow diagram which illustrates the process of making PDO by one embodiment of the invention wherein the heat from the hot vapor stream from the first thermal separator is used to provide heat for the second thermal separator and the heat from the second one is used to provide heat for the first crude PDO separator column to separate the PDO-rich bottoms stream from the water-rich overhead stream.

Hydroformylation of an oxirane, such as ethylene oxide, with hydrogen is one way to provide the 3-hydroxypropanal (3-HPA) mixture of the first step of the process of producing 1,3-propanediol (PDO). 3-hydroxypropanal may also be produced by reaction of acrolein and water under pressure such as described in U.S. Pat. No. 6,284,930.

The oxirane may comprise an organic compound, two carbon atoms of which are connected by an oxy linkage as well as by a carbon-carbon single bond. Suitable oxiranes are described in U.S. Pat. No. 5,463,145. In view of the demand for PDO, ethylene oxide (EO) is the oxirane most preferably used in the process of the invention.

A hydroformylation reaction may provide the 3-hydroxypropanal mixture for use in the process of this invention. This reaction is described in U.S. Pat. No. 5,463,145. The reaction may be carried out in a liquid solvent inert to the reactants and products, i.e., that is not consumed during the reaction. Upon completion of the reaction, the liquid solvent facilitates the separation of the hydroformylation product. The separation may be carried out by allowing the product to form a separate layer, as is disclosed in U.S. Pat. No. 3,687,981. However, as discussed below and described in U.S. Pat. No. 5,463,145, the separation may be carried out by extraction with an aqueous liquid. In general, ideal solvents for the hydroformylation process may (a) exhibit low to moderate polarity such that the 3-hydroxypropanal will be dissolved to a concentration of at least about 5 wt % under hydroformylation conditions, while significant solvent will remain as a separate phase upon extraction with the aqueous liquid, (b) dissolve carbon monoxide, and (c) be essentially non-water-miscible. By "essentially non-water-miscible" is meant that the solvent has a solubility in water at 25° C. of less than about 25 wt % so as to form a separate hydrocarbon-rich phase upon extraction of the 3-hydroxypropanal from the hydroformylation reaction mixture.

Solvents which may be used in the hydroformylation reaction include alcohols and ethers, including methyl-t-butylether, such as those described in U.S. Pat. No. 5,463,145.

As mentioned above, separation of the hydroformylation product mixture (the 3-hydroxypropanal mixture in a non water miscible organic solvent), may be carried out economically most attractively by extraction with an aqueous liquid. Preferably the aqueous liquid is water. The amount of water added to the hydroformylation reaction product mixture may be such as to provide a weight ratio of water:mixture within the range of about 1:1 to about 1:20, preferably about 1:5 to about 1:15. The addition of water at this stage of the reaction may have the additional advantage of suppressing formation of undesirable heavy ends.

Extraction with a relatively small amount of water may provide an aqueous phase which is greater than about 20 wt % 3-hydroxypropanal, preferably greater than about 35 wt % 3-hydroxypropanal, permitting economical hydrogenation of the 3-hydroxypropanal to the 1,3-propanediol. The water extraction may be carried out at a temperature within the range of about 0 to about 75° C., preferably from about 25 to about 55° C., with higher temperatures avoided to minimize condensation products (heavy ends) and catalyst disproportionation to inactive, water-soluble compounds. The water extraction may be carried out under about 0.01 to about 15 MPA, preferably from about 0.5 to about 5 Mpa, of carbon monoxide partial pressure, the preferred range at about 25 to about 55° C. The carbon monoxide may be present in blend with hydrogen, at a composition needed to optimally conduct the hydroformylation reaction.

After separation, the aqueous phase comprising the 3-hydroxypropanal and water may be hydrogenated to yield the 1,3-propanediol by reaction with hydrogen in the presence of a hydrogenation catalyst. Hydrogenation may be carried out in aqueous solution at an elevated temperature during at least a portion of the hydrogenation step of at least about 40° C., generally within the range of about 50 to about 175° C., under a hydrogen pressure of at least about 0.8 MPa, generally within the range of about 1.5 to about 14 MPa. The reaction may be carried out in the presence of a hydrogenation catalyst such as any of those based upon Group VIII metals including nickel, cobalt, ruthenium, platinum and palladium, as well as copper, zinc and chromium and mixtures and alloys thereof. Nickel-based catalysts, including bulk, supported and fixed-bed forms, provide acceptable activities and selectivities at moderate costs. Additional information concerning hydrogenation is provided in U.S. Pat. No. 5,463,145.

The overall process and one specific embodiment of the process may be described with reference to FIG. 1. A 3-hydroxypropanal (HPA) organic solvent mixture 2 is provided to an extraction vessel 4 to which is added an aqueous liquid 6, generally water, for extraction and concentration of the HPA. Liquid extraction may be effected by any suitable means, such as mixer-settlers, packed or trayed extraction columns, or rotating disk contactors. Extraction may, if desired, be carried out in multiple stages. The water-containing 3-hydroxypropanal mixture may be passed to a settling tank (not shown) for resolution into aqueous and organic phases. The aqueous phase 8 is passed to a hydrogenation vessel 12 and reacted with hydrogen 14 in the presence of a hydrogenation catalyst to produce a hydrogenation product mixture 16 which contains PDO, light ends, water and usually also heavy ends (undesirable material having a higher molecular weight than PDO). The reaction solvent 10 can be recycled directly to the reaction step.

Water is separated from the hydrogenation product mixture 16 by introducing the hydrogenation product mixture into a first thermal separation stage 18 and providing heat, for example, by using steam to heat first bottoms sidestream 21 which is then fed directly to the first thermal separation stage 18, to produce a first overhead hot vapor steam 24 comprising water, 1,3-propanediol, and light ends, and a first bottoms thermal separation product mixture 20 comprising water and 1,3-propanediol in greater concentration than the concentration of 1,3-propanediol in the hydrogenation product mixture 16. The first bottoms thermal separation stream 20 is introduced into the second thermal separation stage 26 where additional water is removed in second overhead hot vapor stream 36. First overhead hot vapor steam 24 is introduced into reboiler 32 to heat second bottoms sidestream 30 which is then fed directly to the second thermal separation stage 26 to provide heat for the separation. The condensed vapor stream 34 contains light ends, water, and some traces of PDO and heavy ends. It may be most optimally routed to a light ends removal column 48 for separation of light ends coproduct, and recycle of water and trace PDO and heavy ends back to the extraction section through stream 52.

The second bottoms thermal separation product mixture 28, which comprises PDO in higher concentration than the first bottoms thermal separation product mixture 20, is introduced into crude PDO separator column 38. The second overhead hot vapor stream 36 is introduced to reboiler 44 wherein the heat from hot vapor stream 36 is used to heat crude PDO bottoms sidestream 42 which is then fed directly to separator column 38 to provide heat for the separation in column 38. The condensed vapor stream 45 may contain some light ends and a small amount of PDO and heavy ends. It is optimally routed to the light ends column 48 for removal of light ends (which may comprise ethanol coproduct and possibly hydroformylation solvent). The bottoms from this column may then optimally recycled to extraction as stream 52. The PDO-rich bottoms product mixture 40, which comprises PDO in higher concentration than the second bottoms thermal separation product mixture 28, leaves column 38 and may be further purified to produce 1,3-propanediol.

The crude PDO separator column 38 produces an overhead stream 46 which is a water-rich stream comprising water, about 50 wt % or less PDO (in some embodiments preferably about 2.5 wt % or less), and light ends which may include ethanol, propanol, and hydroformylation solvents. Stream 46 is introduced into the light ends removal column 48, along with other overhead streams from previous thermal separation steps. The light ends removal column 48 produces an overhead stream 50 containing light ends coproduct material including ethanol, and optionally hydroformylation solvents. Further separation of coproducts from reaction solvents may be effected, for recycle of the reaction solvents. The bottoms stream 52 of the light ends removal column 48 may comprise water and about 50 percent or less PDO with trace heavy ends. Stream 52 is then recycled to extraction vessel 4.

Figure 2:
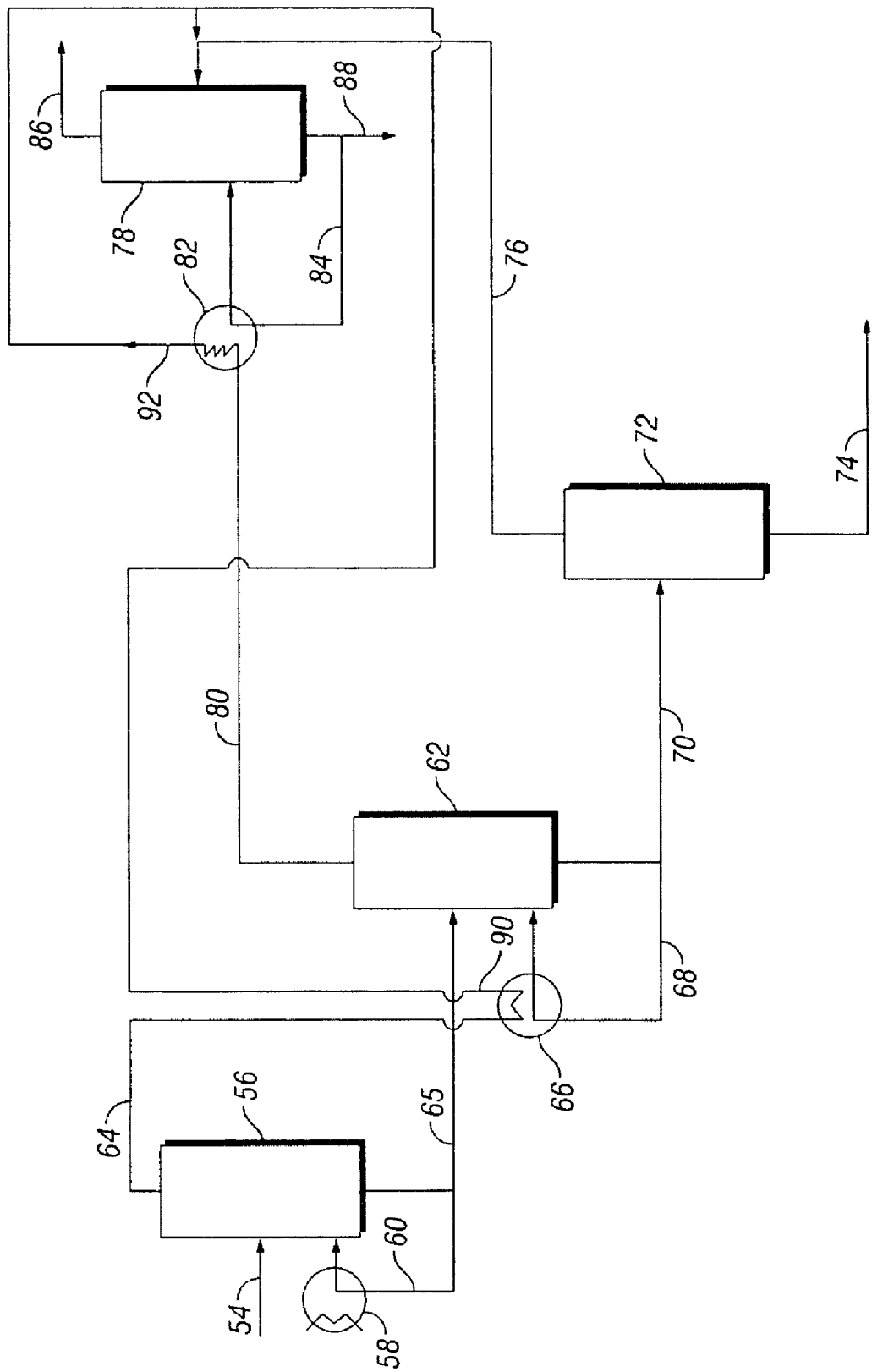
FIG. 2 illustrates another embodiment of the invention wherein there are two thermal separators and the heat from the hot vapor stream from the first thermal separator is used to provide heat for the second thermal separator and the heat from its overhead vapor stream is used to provide heat for the light ends removal column.

FIG. 2 describes another embodiment of the invention. The hydrogenation product mixture 54 is introduced into the first thermal separator 56 which is heated by steam reboiler 58 which heats first bottoms sidestream 60. The first bottoms thermal separation product mixture 65 is introduced into the second thermal separator 62. The first overhead hot vapor stream 64 is directed to reboiler 66 wherein the heat from stream 64 is used to heat the second bottoms sidestream 68 which provides the heat necessary for the second thermal separator 62. The bottom second bottoms thermal separation product mixture 70 is introduced into the PDO crude distillation column 72.

Column 72 separates the PDO-rich bottoms stream 74 from the water-rich crude PDO overhead stream 76 which is then introduced into the light ends removal column 78. The second overhead hot vapor stream 80 may then optionally be introduced into reboiler 82 to heat the light ends removal column bottoms sidestream 84 which then provides the necessary heat to column 78 to separate the light ends in overhead stream 86 from the water-rich bottoms stream 88 which is then recycled to the aqueous liquid extraction step of the process. Alternatively, overhead hot vapor stream 80 may be introduced directly into light ends removal column 78 without heat exchange via a bottoms reboiler such as reboiler 82, whereby it transfers heat directly (to assist in the thermal separation of light ends) at the point of addition to the column 78. If additional heat input is needed to effect the desired separation, then a separate reboiler fired by steam may also be provided on the bottoms of column 78 (not shown).

The condensed vapor from streams 90 and 92 may be routed to the light ends removal column 78. Optionally, vapor feed 90 from reboiler 66 and/or vapor feed 92 from reboiler 82 may be injected directly into column 78 for direct supply of the heat needed for thermal separation. Reboilers 66 and/or 82 may be optionally heated with utility steam, to provide additional heat to supplement the heat available from streams 90 and/or 92, as needed to perform the desired separation in column 78.

Figure 3:
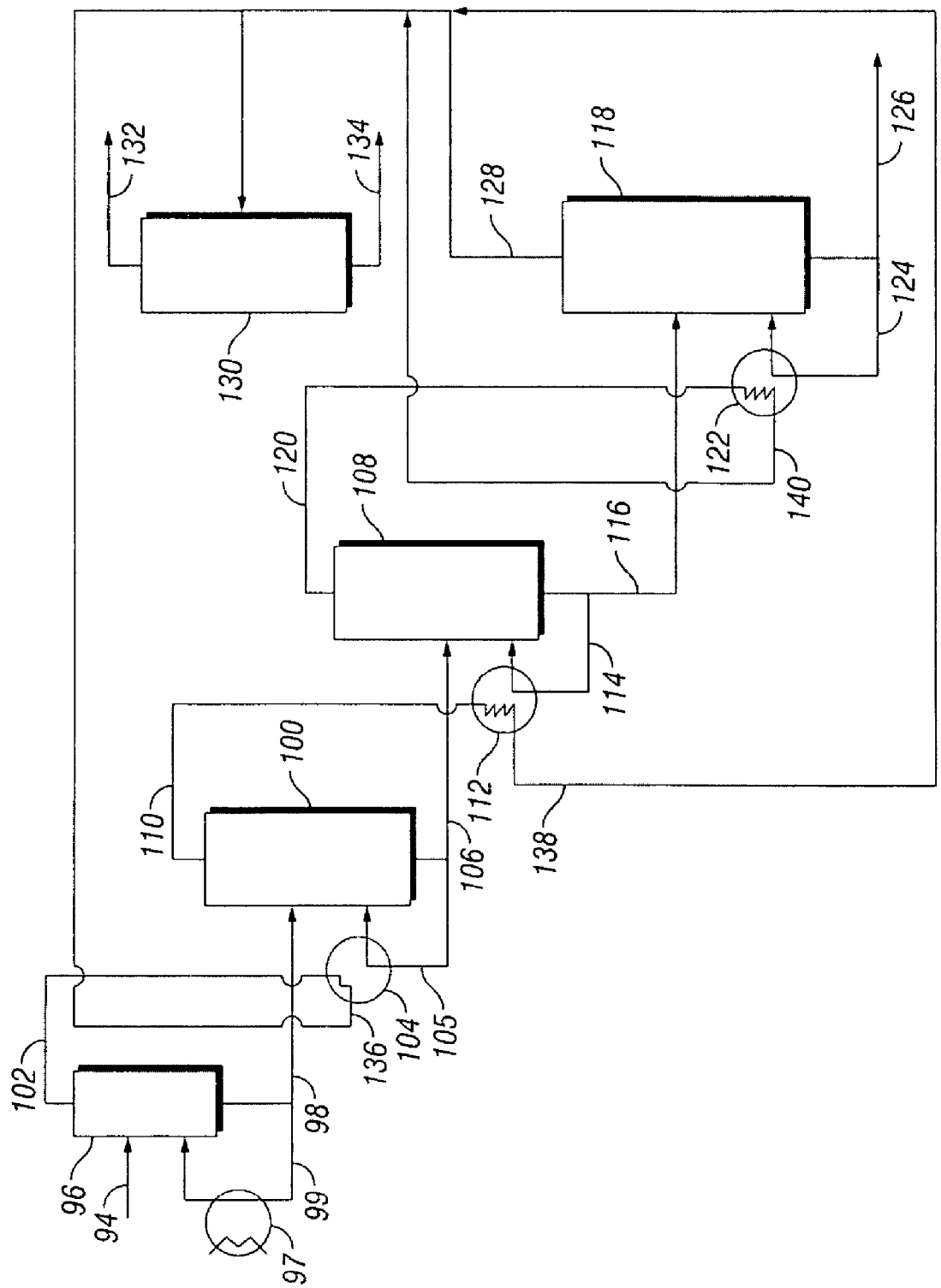
FIG. 3 describes an embodiment of the present invention wherein there are three thermal separators in series and the heat from the hot vapor stream from the first and second thermal separators are used to provide heat for the second and third thermal separators, respectively, and the heat from the hot vapor stream from the third thermal separator is used to provide heat for the crude PDO distillation column.

FIG. 3 illustrates another embodiment of the invention. The hydrogenation product mixture 94 is introduced into the first thermal separation column 96 which is heated by steam reboiler 97 through first bottoms sidestream 99. The first bottoms thermal separation product mixture 98 from column 96 is provided to second thermal separator 100. The first overhead hot vapor stream 102 from column 96 is provided to reboiler 104 wherein its heat is used to heat second bottoms sidestream 105 which provides the heat for the second thermal separator 100. The second bottoms thermal separation product mixture 106 is provided to the third thermal separator 108. The second overhead hot vapor stream 110 is provided to reboiler 112 which heats the third bottoms sidestream 114 from the third thermal separator 108. The third bottoms thermal separation product mixture 116 is provided to crude PDO column 118. The third overhead hot vapor stream 120 is directed to reboiler 122 which heats the crude PDO bottoms sidestream 124 and provides the necessary heat for column 118 to separate the PDO-rich bottom stream 126 from the water-rich overhead stream 128 which is then provided to light ends removal column 130. Column 130 separates the light ends 132 from overhead stream 128 from the water-rich bottom stream 134 which contains PDO for recycle to the aqueous liquid extraction step of the process. The condensed vapor streams 136, 138, and 140 contain water, light ends including ethanol coproduct, and possibly hydroformylation solvents, traces of PDO and heavy ends. These streams may be routed to the light ends removal column 130 to provide heat for separation of light ends from bottoms stream 134, which comprises water with small amounts of PDO and heavy ends and may be optimally recycled to the extraction step.

Figure 4:
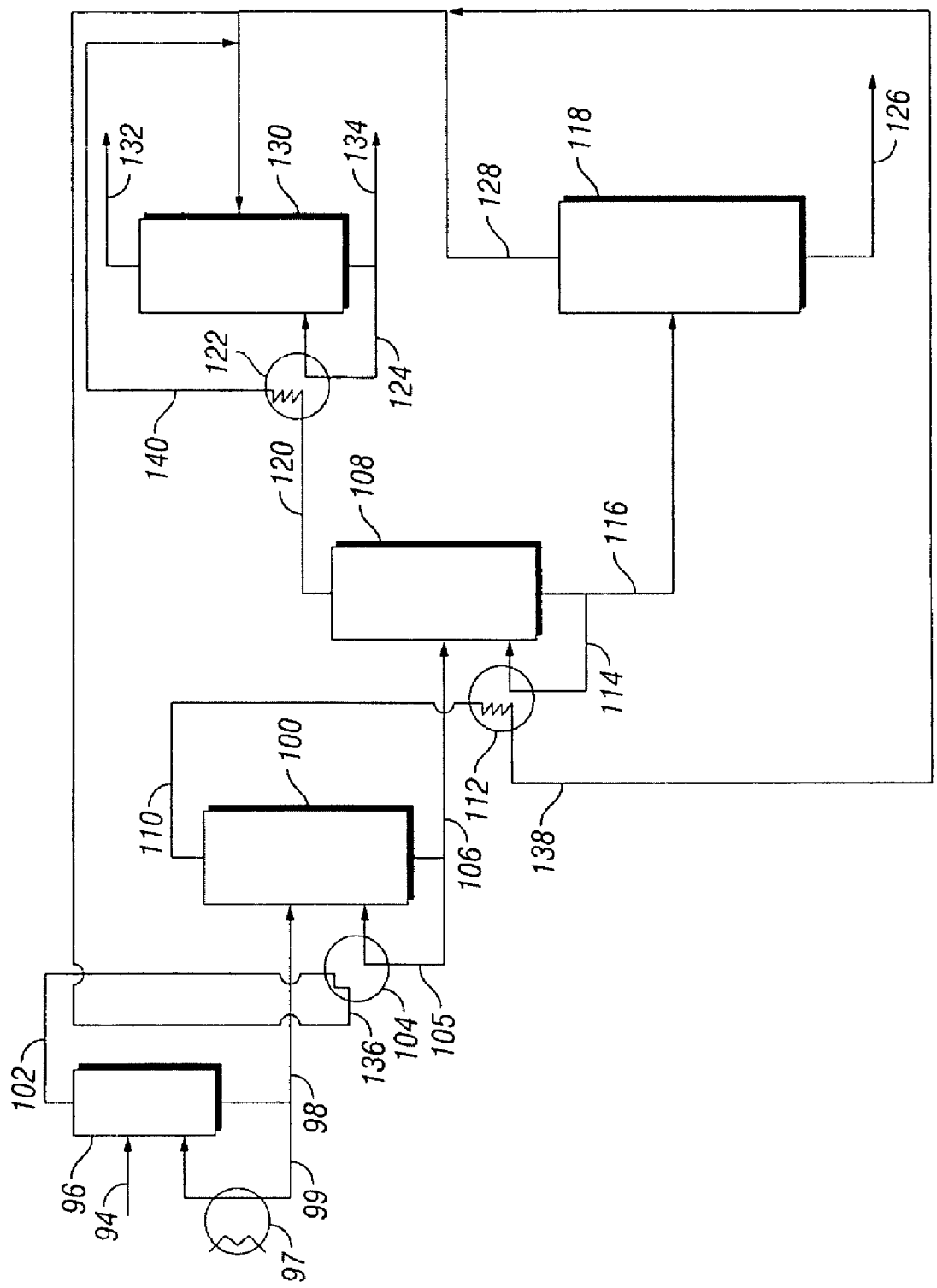
FIG. 4 illustrates an embodiment of the present invention wherein there are three thermal separators and the heat from the hot vapor overhead streams from the first and second thermal separators is used to heat the second and third thermal separators, respectively, and the heat from the hot vapor overhead stream from the third thermal separator is used to heat the distillation for the separation of the recycled water stream containing PDO and the overhead light ends including ethanol.

FIG. 4 illustrates another embodiment of the present invention. The embodiment is the same as the embodiment of FIG. 3 except that reboiler 122 heats sidestream 124 which provides heat for the separation in light ends removal column 130. As with the case of reboiler 82 in FIG. 2, reboiler 122 may be eliminated and overhead hot vapor stream 120 could be directly introduced into column 130. If additional heat is required a steam reboiler could be used.

The thermal separation stages may be selected from distillation, flashing, evaporation, stripping, etc., or a combination of these. In one embodiment of the invention, at least two of the thermal separation stages act together as a multi-effect evaporator.

Generally, the amount of PDO in the water-rich stream recycled to the extraction step is about 50 wt % or less, about 25 wt % or less, about 10 wt % or less, or about 2.5 wt % or less if the unit design has a low capacity for removal and optional recycle of hydroformylation catalyst. Higher concentrations of PDO may be recycled to extraction, but may result in higher losses of hydroformylation catalyst into the aqueous extract mixture, requiring increased capacity for removal and optional recycle of hydroformylation catalyst. Recycle of PDO with water to the extraction step further reduces the cost of energy to remove water from final product, however, in addition to the benefits provided by the current invention. The relative benefits of low hydroformylation catalyst loss rates at higher water content/lower PDO fractions in the extraction feed may be optimized relative to the higher cost of water removal.

The use of multi-effect evaporation to reduce process energy requirements for water or solvent removal invariably results in some PDO appearing in flashed overhead streams. Any PDO thus appearing in the combined overhead streams from multi-effect evaporation and water removal steps is recycled to extraction, as any further purification of the recycle stream to separate PDO from water would offset the energy savings realized by implementing the multi-effect concept. Ethanol and other reaction byproducts lighter than PDO must be separated from this recycle stream to prevent accumulation in the recycle loop. This can be done without excessive energy penalty because they are more volatile than water.

In an embodiment of the invention wherein multiple-effect evaporation stages are utilized, the pressure may be decreased from the first thermal separator to the second thermal separator and from the second to the third thermal separator, etc. This step down pressure technique is advantageous because 1) the hydrogenation product mixture comes from a high pressure vessel as needed to optimize the conversion in hydrogenation, and 2) the step-down approach avoids the need to provide additional equipment to recompress the vapor in order to again transfer heat to another stage or effect. Steam and or sensible heat of the hydrogenation product may be used to heat the first effect (thermal separation stage) and then the hot vapor stream from each effect is used to heat the next effect. The so-called steam economy of the multi-effect evaporator scheme increases in proportion to the number of effects. Thus, referring to FIG. 3, the first effect (thermal separator 96) may be operated at a pressure from that used in the hydrogenation step to about 15,000 kPa, preferably at a lower pressure but above about 101 kPa to reduce the cost of equipment, while maintaining a pressure high enough to provide heat transfer at the temperature required for subsequent thermal separation. In the absence of vapor recompression, the pressure in the second effect (thermal separator 100) will be lower than that in the first effect, i.e., from about 500 to about 2500 kPa, and the pressure in the subsequent effects will be successively lower. A sequence of 1400, 500, and 150 kPa was found to be effective in introducing two effects to the removal of water from a mixture of 30% PDO in water. This pressure staging approach allows heat to be provided to subsequent stages at the temperature required to effect the desired thermal separation. Since the temperature required to boil the bottoms mixture increases as water is removed from PDO, it is advantageous in a multi-effect concept to operate upstream water removal stages at higher pressures, so that water and solvent vapors can be condensed at the higher temperature needed to provide heat to subsequent water removal steps. Alternately, the vapor from an upstream effect may be recompressed to obtain the higher temperature needed to effect further water removal.

The step down pressure method described above is only one method which can be used in the process of the present invention to utilize the heat created in the process to heat successive thermal separation steps or other steps in the process. One example of another method is mechanical recompression. This involves re-compression of the overhead vapor such that it can be condensed and transfer heat at temperature which is high enough to effect the desired thermal separation of heating of a subsequent operation. Also, a steam ejector can be used.

It is preferred that a multiple effect evaporation scheme be utilized to remove water from the hydrogenation product mixture. In this multiple effect evaporator scheme, steam from an outside source is condensed in the heating element of the first effect which may be the first reboiler or a heat exchanger used to preheat the feed. The first effect may operate at a higher temperature and pressure than that used in the subsequent effects. The evaporated water, which in the above description is part of the overhead hot vapor stream, serves as the heating medium for the second effect. The pressure and temperature of the evaporated water may be lower than in the column bottoms, but sufficiently high to efficiently remove more water via further thermal separation of the PDO-rich stream from the bottom of the first effect. The evaporated water from the second effect may then serve as the heating medium for a third effect which may be operated at an even lower temperature and pressure. Additional effects may be added.

As described in more detail above, the bottoms stream from a previous effect, which contains a partially concentrated PDO-rich mixture, is introduced to a crude PDO separator column wherein the bottoms stream therefrom is a very highly concentrated PDO-rich stream which can then be further processed to remove more water and light and heavy ends that may still be contained therein. This column comprises the last effect in the thermal separation sequence when heated via condensing vapor from an upstream separation. The overhead stream from the crude PDO separator column is a water-rich stream which may contain 50 wt % or less PDO and also contains water and light ends including ethanol and one or more hydroformylation solvents. If a sufficient number of distillation stages are provided for this column, the overhead stream may optionally be relatively dilute in PDO, such as 25 weight percent or less, and typically 10 wt % or less, and even as low as 2.5 wt % or less. This stream is introduced into a light ends removal column which separates the light ends from the bottoms stream containing mostly water and PDO. This bottoms stream is recycled to the aqueous liquid extraction step of the process. The condensate from the various effects are also typically combined into the feed to the light ends column in order to recycle water for extraction after removal of light coproducts and hydroformylation solvents.

The optimal PDO process described in U.S. Pat. No. 5,463,145 requires high purity water in the feed to the extraction section. High purity water may not be produced if heat is recovered via multieffect evaporation as in the process of the current invention. Implementation of the heat recovery schemes comprising the current invention will result in larger amounts of PDO recycled to the extraction section. Small amounts of PDO (about 25 weight percent or less, preferably about 2.5 weight percent or less) can be tolerated in the recycle water, depending upon the capacity present for removal and optional recycle of hydroformylation catalyst which is lost to aqueous extract at increasing concentrations as PDO content of the extraction water is increased. Removal of light alcohols from the recycle water stream may be important to maintain optimal solvent polarity in the hydroformylation solvent, depending upon the solvent chosen, because the light alcohols (which may form at least a part of the light ends) may be carried over to the hydroformylation stage when the organic phase containing the hydroformylation catalyst is recycled to the hydroformylation stage. PDO may also be carried over to the hydroformylation stage in this manner. When some solvents are used, the presence of PDO can cause problems by increasing polarity to allow disproportionation of active catalyst to inactive species, such as is the case when methyl t-butyl ether is used as primary solvent. The presence of light ends can also adversely affect the hydroformylation catalyst. For this reason, the light ends coproduct may be first removed as described above before the water/PDO stream is recycled to the extraction step.

The process of this invention has modified the water balance and process synthesis of the process described in the aforementioned U.S. patent to lower the process cost by effectively recovering and reusing heat added to separate and recycle water. This process recovers and reuses heat that is effectively added at the crude column reboiler in the prior art process. By adding a smaller amount of heat upstream in a multieffect configuration and reusing it, energy is saved.

EXAMPLES

Figure 5:
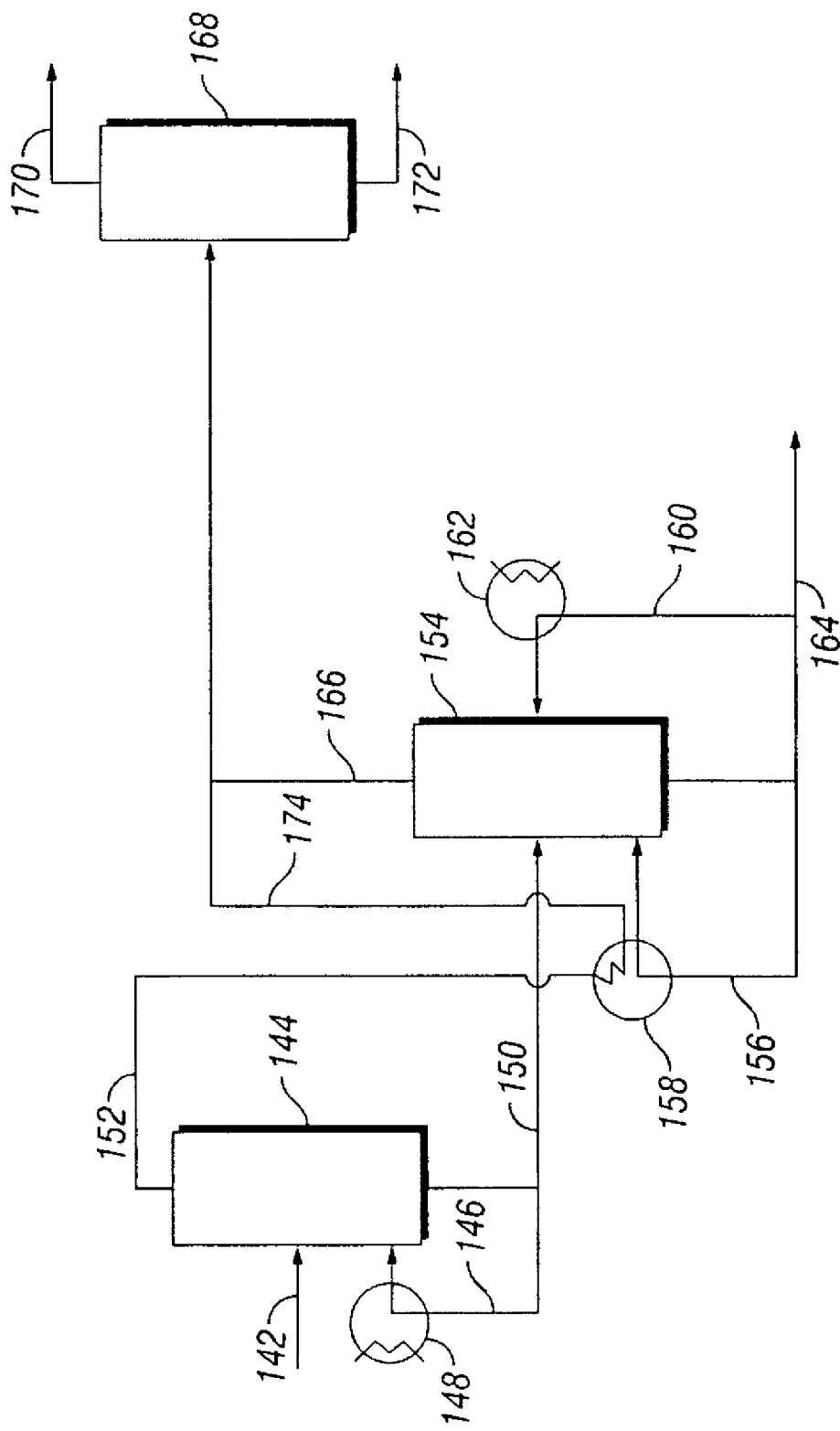
FIG. 5 illustrates the embodiment described in the example wherein one thermal separation stage and the crude PDO distillation column are the effects of multi-effect evaporation.

Referring to FIG. 5, a hydrogenation product mixture 142, which comprises 25 wt % PDO and water, is directed to a 200 psi (1.4 MPa) flasher 144. Flasher bottom sidestream 146 is heated by reboiler 148 which is heated by steam. Flasher bottoms stream 150, which comprises 40 wt % PDO and water, is directed to crude PDO column 154. Overhead hot vapor stream 152 from flasher 144 is directed to reboiler 158 which heats crude PDO column sidestream 156 to provide heat for column 154. Steam reboiler 162 may be used to heat crude PDO column sidestream 160 to provide additional heat for column 154.

PDO-rich bottoms stream 164 from column 154, which comprises PDO and about 15 wt % water, may be further processed to increase the purity of the PDO. Water-rich crude PDO column overhead stream 166, which comprises water, light ends including ethanol, and less than 2.5 wt % PDO, is directed to light ends removal column 168. Condensed vapor stream 174 which comprises water, light ends including ethanol, and about 2.5 wt % PDO, is combined with overhead stream 166 and provided to light ends removal column 168. Column 168 separates the light ends, including ethanol, in overhead stream 170 from water-rich bottoms stream 172 which comprises water and about 1.25 wt % PDO. Bottoms stream 172 is then recycled to the aqueous liquid extraction step of the process.

The crude column employs 7 stages with structured packing. 2-12 stages could be used in a trayed or packed column, or with structured packing. The bottoms temperature is typically run in the range of 130 to 170° C. but could be run in the range of about 120 to about 180° C., most preferably about 160° C. The column is operated at slightly above ambient pressure (101 to 150 kPa absolute). A small reflux (1:1 vs. overhead product) may be employed to further improve the separation of PDO from water.

The light ends removal column has 20 theoretical stages, obtained by using dumped packing (i.e., a packed column) to effect separation and recycle of hydroformylation solvent, coproduct ethanol and sometimes propanol and other light alcohols, and water. However, 10-30 theoretical stages could be used. Separation of ethanol from water is only partially effective unless steps are taken to break the azeotrope involved in this separation. Such steps are known to those skilled in the art and may include use of entraining agents, pressure swing, or use of driers such as molecular sieves, membranes, or other means to complete the removal of water from ethanol. An approximate mixture of 85 weight percent ethanol and 15 weight percent water and small amounts of additional alcohol coproducts such as propanol is removed overhead in a column of 20 theoretical stages which is operated at a bottoms temperature of 115° C., and a total pressure of slightly above ambient pressure (101–150 kPa).

We claim:

1. A process for preparing a 1,3-alkanediol from a 3-hydroxyaldehyde, comprising providing a mixture of a 3-hydroxyaldehyde in an organic solvent; extracting into an aqueous liquid a major portion of the 3-hydroxyaldehyde to provide an aqueous phase comprising the 3-hydroxyaldehyde in greater concentration than the concentration of the 3-hydroxyaldehyde in the 3-hydroxyaldehyde mixture, and an organic phase; separating the aqueous phase from the organic phase; contacting the aqueous phase with hydrogen in the presence of a hydrogenation catalyst to provide a hydrogenation product mixture comprising a 1,3-alkanediol and water; separating water from the 1,3-alkanediol using a multi-effect evaporation scheme; recycling water containing 50 wt % or less of the 1,3-alkanediol based upon the total amount of 1,3-alkanediol and water to the extraction stage; and recovering the 1,3-alkanediol.

2. The process of claim 1 wherein light ends are removed from the water containing 50 wt % or less of the 1,3-alkanediol before it is recycled.

3. A process for preparing 1,3-propanediol comprising the steps of:
   (a) providing a mixture of 3-hydroxypropanal in an essentially non water miscible organic solvent;
   (b) adding an aqueous liquid to said mixture and extracting into said aqueous liquid a major portion of the 3-hydroxypropanal to provide an aqueous phase comprising 3-hydroxypropanal in greater concentration than the concentration of 3-hydroxypropanal in the 3-hydroxypropanal mixture, and an organic phase;

(c) separating the aqueous phase from the organic phase;
(d) contacting the aqueous phase with hydrogen in the presence of a hydrogenation catalyst to provide a hydrogenation product mixture comprising 1,3-propanediol, water, and light ends;
(e) separating water from the hydrogenation product mixture by introducing the hydrogenation product mixture into a first thermal separation stage and heating it to produce a first overhead hot vapor stream comprising water and light ends and a first bottoms thermal separation product mixture stream comprising water and 1,3-propanediol in greater concentration than the concentration of 1,3-propanediol in the hydrogenation product mixture;
(f) introducing the first bottoms thermal separation product mixture stream into a second thermal separation stage to produce a second overhead hot vapor stream comprising water and light ends and a second bottoms thermal separation product mixture stream comprising water and 1,3-propanediol in greater concentration than the concentration of 1,3-propanediol in the first bottoms thermal separation product mixture stream;
(g) optionally repeating step f) at least once to produce a third or successive overhead hot vapor stream comprising water and light ends and a third or successive bottoms thermal separation product mixture stream comprising water and 1,3-propanediol in greater concentration than the concentration of 1,3-propanediol in the preceding bottoms thermal separation product mixture stream;
(h) removing the heat from at least one of the overhead hot vapor streams and providing said heat for use in at least one of the other steps of the process for preparing 1,3-propanediol;
(i) recycling the water from the overhead hot vapor streams to step (b); and
(j) recovering 1,3-propanediol.

4. A process for preparing 1,3-propanediol comprising the steps of:
(a) providing a mixture of 3-hydroxypropanal in an essentially non water miscible organic solvent;
(b) adding an aqueous liquid to said mixture and extracting into said aqueous liquid a major portion of the 3-hydroxypropanal to provide an aqueous phase comprising 3-hydroxypropanal in greater concentration than the concentration of 3-hydroxypropanal in the 3-hydroxypropanal mixture, and an organic phase;
(c) separating the aqueous phase from the organic phase;
(d) contacting the aqueous phase with hydrogen in the presence of a hydrogenation catalyst to provide a hydrogenation product mixture comprising 1,3-propanediol, water, and light ends;
(e) separating water from the hydrogenation product mixture by introducing the hydrogenation product mixture into a first thermal separation stage and heating it to produce a first overhead hot vapor stream comprising water and light ends and a first bottoms thermal separation product mixture stream comprising water and 1,3-propanediol in greater concentration than the concentration of 1,3-propanediol in the hydrogenation product mixture;
(f) introducing the first bottoms thermal separation product mixture stream into a second thermal separation stage to produce a second overhead hot vapor stream comprising water and light ends and a second bottoms thermal separation product mixture stream comprising water and 1,3-propanediol in greater concentration than the concentration of 1,3-propanediol in the first bottoms thermal separation product mixture stream;
(g) optionally repeating step f) at least once to produce a third or successive overhead hot vapor stream comprising water and light ends and a third or successive bottoms thermal separation product mixture stream comprising water and 1,3-propanediol in greater concentration than the concentration of 1,3-propanediol in the preceding bottoms thermal separation product mixture stream;
(h) removing the heat from at least one of the overhead hot vapor streams and providing said heat for use in at least one of the other steps of the process for preparing 1,3-propanediol;
(i) introducing the last bottoms thermal separation product mixture stream to a crude 1,3-propanediol separator to produce a crude 1,3-propanediol overhead stream comprising water, 1,3-propanediol, and light ends, and a crude 1,3-propanediol bottoms stream comprising water and 1,3-propanediol in greater concentration than the concentration of 1,3-propanediol in the last bottoms thermal separation product mixture stream;
(j) introducing the crude 1,3-propanediol overhead stream into a light ends separator to remove light ends from the water and 1,3-propanediol, thereby producing a concentrated water stream containing 50 wt % or less 1,3-propanediol based upon the total amount of 1,3-propanediol and water;
(k) recycling the concentrated water stream to step b); and
(l) recovering 1,3-propanediol from the crude 1,3-propanediol bottoms stream.

5. The process of claim 4 wherein heat removed from the first overhead vapor stream is used to provide at least part of the heat necessary for thermal separation step (f).

6. The process of claim 5 wherein heat removed from the second overhead vapor stream is used to provide at least part of the heat necessary for thermal separation step (g).

7. The process of claim 4 wherein heat removed from at least one of the overhead vapor streams is used to provide at least part of the heat necessary for thermal separation step (g).

8. The process of claim 4 wherein heat removed from at least one of the overhead hot vapor streams is used to provide at least part of the heat necessary for the separation of step (i).

9. The process of claim 8 wherein heat removed from the first overhead vapor stream is used to provide at least part of the heat necessary for thermal separation step (f).

10. The process of claim 9 wherein heat removed from the second overhead vapor stream is used to provide at least part of the heat necessary for thermal separation step (g).

11. The process of claim 4 wherein heat removed from at least one of the overhead hot vapor streams is used to provide at least part of the heat necessary for the separation of step (j).

12. The process of claim 11 wherein heat removed from the first overhead vapor stream is used to provide at least part of the heat necessary for thermal separation step (f).

13. The process of claim 12 wherein heat removed from the second overhead vapor stream is used to provide at least part of the heat necessary for thermal separation step (g).

14. The process of claim 4 wherein heat removed from at least one of the overhead hot vapor streams is used to provide at least part of the heat necessary for step (l).

15. The process of claim 4 wherein heat removed from at least one of the overhead hot vapor streams is used to provide at least part of the heat necessary for step (d).

16. The process of claim 4 wherein heat removed from at least one of the overhead hot vapor streams is used to provide at least part of the heat necessary for step (e).

17. The process of claim 4 wherein the pressure is decreased from one thermal separator to the next.

18. The process of claim 4 wherein at least some of the thermal separators are multi-effect evaporators.

19. The process of claim 4 wherein step h) is carried out by removing the heat from at least one of the overhead hot vapor streams and providing said heat for use in at least one of the other steps of the process for preparing 1,3-propanediol by heat exchange with a lower temperature process stream and/or by accompanying transfer of latent heat by condensation.

20. The process of claim 4 wherein the concentrated water stream contains 50 wt % or less 1,3-propanediol.

21. The process of claim 20 wherein the concentrated water stream contains 25 wt % or less 1,3-propanediol.

22. The process of claim 21 wherein the concentrated water stream contains 10 wt % or less 1,3-propanediol.

23. The process of claim 22 wherein the concentrated water stream contains 2.5 wt % or less 1,3-propanediol.

24. A process for preparing 1,3-propanediol comprising the steps of:
  (a) providing a mixture of 3-hydroxypropanal in an essentially non water miscible organic solvent;
  (b) adding an aqueous liquid to said mixture and extracting into said aqueous liquid a major portion of the 3-hydroxypropanal to provide an aqueous phase comprising 3-hydroxypropanal in greater concentration than the concentration of 3-hydroxypropanal in the 3-hydroxypropanal mixture, and an organic phase;
  (c) separating the aqueous phase from the organic phase;
  (d) contacting the aqueous phase with hydrogen in the presence of a hydrogenation catalyst to provide a hydrogenation product mixture comprising 1,3-propanediol, water, and light ends;
  (e) separating water from the hydrogenation product mixture by introducing the hydrogenation product mixture into a thermal separation stage and heating it to produce an overhead hot vapor stream comprising water and light ends and a bottoms thermal separation product mixture stream comprising water and 1,3-propanediol in greater concentration than the concentration of 1,3-propanediol in the hydrogenation product mixture;
  (f) removing the heat from the overhead hot vapor stream and providing said heat for use in a crude 1,3-propanediol distillation column wherein the overhead hot vapor stream is condensed;
  (g) introducing the bottoms thermal separation product mixture stream to the crude 1,3-propanediol separator to produce a crude 1,3-propanediol overhead stream comprising water, 1,3-propanediol, and light ends, and a crude 1,3-propanediol bottoms stream comprising water and 1,3-propanediol in greater concentration than the concentration of 1,3-propanediol in the bottoms thermal separation product mixture stream;
  (h) introducing the crude 1,3-propanediol overhead stream into a light ends separator to remove light ends from the water and 1,3-propanediol, thereby producing a concentrated water stream containing 50 wt % or less 1,3-propanediol based upon the total amount of 1,3-propanediol and water;
  (i) recycling the concentrated water stream to step b); and
  (j) recovering 1,3-propanediol from the crude 1,3-propanediol bottoms stream.

25. The process of claim 24 wherein step f) is carried out by heat exchange with the bottoms thermal separation product mixture stream and/or by accompanying transfer of latent heat by condensation.

26. The process of claim 24 wherein the concentrated water stream contains 25 wt % or less 1,3-propanediol.

27. The process of claim 26 wherein the concentrated water stream contains 10 wt % or less 1,3-propanediol.

28. The process of claim 27 wherein the concentrated water stream contains 2.5 wt % or less 1,3-propanediol.

* * * * *